United States Patent [19]

Galef, Jr. et al.

[11] Patent Number: 4,861,585
[45] Date of Patent: Aug. 29, 1989

[54] ENHANCED RODENT EDIBLE WITH NATURAL ATTRACTANTS

[75] Inventors: Bennett G. Galef, Jr., Dundas, Canada; J. Russell Mason, Philadelphia, Pa.

[73] Assignee: Monell Chemical Senses Center, Philadelphia, Pa.

[21] Appl. No.: 247,899

[22] Filed: Sep. 22, 1988

Related U.S. Application Data

[63] Continuation of Ser. No. 922,185, Oct. 23, 1985, abandoned.

[51] Int. Cl.[4] ............................................. A01N 25/00
[52] U.S. Cl. ...................................................... 424/84
[58] Field of Search ........................................... 424/84

[56] References Cited

PUBLICATIONS

Galef et al., "Aversive and Attractive Marking of Toxic and Safe Foods by Norway Rats", *Behavioral and Neural Biology*, vol. 43, pp. 299–309 (1985).

Galef et al., "Transfer of Information Concerning Distant Foods: A Laboratory Investigation of the 'Information–Centre' Hypothesis", *Animal Behavior*, 31:748–758 (1983).

Galef et al., "Transfer of Information Concerning Distant Foods in Rats: A Robust Phenomena", *Animal Learning & Behavior*, 12(3):292–296 (1984).

Galef et al., "Demonstrator Influence on Observer Diet Preference Analyses of Critical Social Interactions and Olfactory Signals", *Animal Learning & Behavior*, 13:31–38 (1985).

Galef et al., "Delays After Eating: Effects on Transmission of Diet Preferences and Aversions", *Animal Learning & Behavior*, 13:39–43 (1985).

Galef et al., "Demonstrator Influence on Observer Diet Preference: Effects of Simple Exposure and the Presence of a Demonstrator", *Animal Learning & Behavior*, 13:25–30 (1985).

Galef et al., "Social Identification of Toxic Diets by Norway Rats" (R. norvegicus), *Journal of Comparative Psychology*, (in press).

Galef et al., "Aversive and Attractive Marking of Toxic and Safe Foods by Norway Rats", *Behavioral and Neural Biology*, 43:298–310 (1985).

Galef, "Utilization by Norway Rats (R. norvegicus) of Multiple Messages Concerning Distant Foods", *Journal of Comparative Psychology*, 97(4):364–371 (1983).

*Primary Examiner*—Douglas W. Robinson
*Assistant Examiner*—Roger Gobrogge
*Attorney, Agent, or Firm*—Woodcock Washburn Kurtz Mackiewicz & Norris

[57] ABSTRACT

A novel rodent edible is disclosed. The edible contains a conventional edible component, and an attractant naturally present in the breath of said rodents in an amount effective to increase the preference for said edible component to said rodents. Carbon disulfide and carbonyl sulfide are the preferred attractants. Preference for the edible component may be achieved by mixing the attractant with the food, or merely by associating the aroma of the attractant with the edible component to stimulate a preference for that component.

5 Claims, 2 Drawing Sheets

ENHANCED RODENT EDIBLE WITH NATURAL ATTRACTANTS

This is a continuation of application Ser. No. 922,185, filed Oct. 23, 1986, now abandoned.

BACKGROUND OF THE INVENTION

The present invention relates to the field of rodent edibles, and more particularly to rodent foods and rodenticides which are voluntarily ingested by rodents and which are intended to limit or diminish the population thereof by death, sterilization, or otherwise.

Considerable work has been conducted on the feeding and food preference habits of various rodents, particularly rats and mice. It has long been known that rodents transfer information concerning foods they have ingested, although prior investigators have not determined what mechanism is responsible for such information transfer. In Galef et al, "Transfer of Information Concerning Distant Foods: A Laboratory Investigation of the 'Information-Centre' Hypothesis", *Animal Behavior*, 31: 748–758 (1983), "observer" rats are disclosed as preferring a diet previously eaten by a "demonstrator" conspecific with whom the observer has interacted prior to making its choice between diets. Galef et al disclose the demonstrator influence on observer diet selection is maintained even if, during the period of demonstrator-observer interaction, the demonstrator is anesthetized and a wire-mesh barrier prevents the demonstrator from physically contacting the observer. Demonstrator influence on observer diet choise is blocked by either rendering the observer anosmic or placing a transparent plexiglass barrier between demonstrator and observer during their period of interaction. Galef et al thus concluded that olfactory cues passing from the demonstrator to the observer provide observers with information concerning the demonstrators' diets and that these olfactory cues are sufficient to bias diet selection by the observers.

In Galef et al, "Transfer of Information Concerning Distant Food in Rats: A Robust Phenomenon", *Animal Learning and Behavior*, 12(3): 292–296 (1984), an observer rat's diet preference for the diet eaten by a demonstrator was reported for first-generation laboratory bred wild rats as well as domesticated rats; food-deprived as well as non-deprived observers; unfamiliar as well as familiar demonstrator-observer pairs; both 21 day old and adult observers; and rats selecting fluids as well as solids for ingestion. These data were reported as indicating that the social transmission of information concerning distant diets is a general and robust phenomenon, observable under a wide variety of experimental conditions.

Galef et al, "Demonstrator Influence on Observer Diet Preference: Effects of Simple Exposure in the Presence of a Demonstrator", *Animal Learning and Behavior*, 13: 25–30 (1985) reports that observer experience of diet-related cues in the stimulus context provided by the presence of a demonstrator was sufficient to enhance observer preference for a diet, where simple exposure to that diet was not. Galef et al report that demonstrator-induced changes in observer preference could be explained by a number of hypotheses, one of which is that the effective olfactory cue passing from the demonstrator to the observer is simply the smell of the food a demonstrator has contacted and ingested. Alternatively, Galef et al hypothesize that the demonstrator-emitted cue that is effective in altering the diet preference of an observer is a combination of the smell of demonstrator-ingested diet and some demonstrator-produced "signal". In a series of experiments intended to test these hypotheses See Galef et al., "Demonstrator Influence on Observer Diet Preference: Analyses of Critical Social Interactions and Olfactory Signals", *Animal Learning & Behavior*, 13: 31–38 (1985), observer rats were caused to interact with anesthetized demonstrators whose faces had been rolled in a particular diet. In subsequent simultaneous choice tests between that diet and another diet, the observer rat preferred the diet in which the demonstrator's face was rolled. In another experiment, observer rats were caused to interact with a demonstrator freshly killed by anesthetic overdose, whose face was rolled in a particular diet. In a subsequent choice between diets, including the particular diet, the observer was indifferent. In a further reported experiment, an observer rat interacted with a surrogate rate (a roll of cotton batting) one end of which was rolled in a particular diet. In a subsequent choice between that diet and another diet, the observer was indifferent. In a further experiment, either the hind quarters or the faces of demonstrators were rolled in the particular diet prior to presentation to the observers. The observers that had interacted with powdered-rear demonstrators ingested significantly less of the respective demonstrators' diets than those observers that had interacted with powdered-face demonstrators. Galef et al conclude that the demonstrator influence on observer diet preferences was not the consequence of simple exposure of observers to demonstrator-emitted cues reflecting demonstrators' diet.

In Galef et al, "Delays After Eating: Effects on Transmission of Diet Preferences and Aversions", *Animal Learning and Behavior*, 13: 39–43 (1985), Galef et al report that for at least four hours after ingestion, demonstrator rats emit diet related cues sufficient to alter an observers' diet preference. Diet related cues emitted by demonstrators for one to two hours after a meal were adequate conditional stimuli for aversion learning by observers. In "Utilization by Norway Rats of Multiple Messages Concerning Distant Foods", *Journal of Comparative Psychology*, 97: 364–371 (1983) Galef demonstrated that once an observer and demonstrator have interacted, the observer can use information acquired from a demonstrator as much as 12 hours later in selecting a diet. Accordingly, this more recent paper suggests that information concerning the diet of a demonstrator may effect an observers preference for as long as 16 hours after the time of the demonstrators initial ingestion of the food.

More recently, in a manuscript currently in press entitled "Social Identification of Toxic Diets by Norway Rats (*R. norvegicus*)", *Journal of Comparative Psychology*, (1986), Dr. Galef reports on experiments involving naive rats who interacted with two demonstrators who had recently eaten a diet unfamiliar to the observer. The observer then ate two unfamiliar diets in succession, one of which was the food its demonstrators had eaten. The observer was then subjected to toxicosis and again was offered a simultaneous choice between the two diets it had eaten prior to toxicosis induction. During the choice test, observers exhibited an aversion to that diet their respective demonstrators had not eaten. The results indicate that exposure of a rat to conspecifics that have eaten a diet can act, as does actual ingestion of a diet, to reduce the diet's subsequent associability with toxicosis.

Each of the above-identified Galef and Galef et al papers are hereby incorporated by reference as though fully set forth herein.

In addition to the information conveyed as a result of demonstrator-observer interactions, it is also known that rodents tend to prefer to eat food which has already been partially consumed by their conspecifics. This phenomenon occurs whether or not the individual has had direct contact with a demonstrator conspecific, provided the food in question has quite recently been partially consumed. See Galef and Beck, "Aversive and Attractive Marking of Toxic and Safe Foods by Norway Rats", *Behavioral and Neural Biology*, 43: 298-310 (1985).

Accordingly, while considerable research has been conducted and much information exists concerning rodent food preferences, the literature in this field has yet to identify whether a specific chemical or olfactory signal is generated by one rodent which is used or relied upon by another in making food preference decisions. Nor, if such signal exists, has the art identified what that signal is.

The present invention also relates to the field of volatile sulfur compounds. Volatile sulfur compounds are known to be present in human breath, and have been identified as a major source or halitosis. In other contexts, liquids or syrups smelling like rotten eggs (probably containing hydrogen sulfide) have been used as repellents for certain wildlife, particularly deer. These liquids or syrups were used in bottles having wicks placed near deer marking spots, as for example, in orchards, for the purpose of repelling deer. More recently, materials smelling like rotten eggs have been used as coyote lures in combination with traps or explosive devices intended to control coyote populations.

SUMMARY OF THE INVENTION

Applicants have discovered that rodents generate a chemical signal which is relied upon by other conspecifics in selecting food which is or has recently been associated with that signal. More particularly, applicants have shown that certain volatile sulfur compounds, particularly carbon disulfide, which are naturally present in rat breath, act as rodent food "attractants", i.e., material causing a rodent to choose to ingest and/or cache an edible for later consumption. Accordingly, the present invention provides a novel rodent edible for feeding to rodents, which comprises an edible component, such as a food, poison or medicament, and an attractant present in the breath of said species in an amount which is effective to increase the preference of that edible component to said species. The preferred attractants are the sulfur containing compounds carbon disulfide and carbonyl sulfide, the former of which is preferred because it is not a gas at room temperature. In the preferred embodiment, the edible component is a poison, a medication (sterilant), or a food.

The present invention also provides a novel method for conditioning a rodent to prefer a selected rodent edible, comprising the steps of providing samples of a rodent edible and an attractant naturally present in the breath of such rodents, and exposing the rodent to be conditioned to combined amounts of the edible and the attractant sufficient to condition the rodent to preferentially select the edible.

Accordingly, a primary object of the present invention is a provision of a rodent edible which is naturally preferred by rodents which have no prior experience therewith.

A further object of the present invention is the provision of a novel method of conditioning a rodent to prefer a selected rodent edible.

These and other objects of the present invention will become apparent from the following, more detailed description.

DETAILED DESCRIPTION OF THE INVENTION

The present invention relates to methods of artificially causing a rodent to exhibit a given preference for a rodent edible with which he may have no prior experience. As used herein, rodent edibles and edible components are any of the components which are known or may be developed for feeding to rodents, particularly rats and mice. Such rodent edibles presently include rodent baits, bait formulations, feed, liquids, medications such as sterilants tracking powders, etc., which are presented or applied for voluntary ingestion by rodents.

When the edible itself is to be treated so that it is more attractive to the rodents, the edible will comprise an edible component, and an attractant present in the breath of the rodents in an amount which is effective to increase the rodents' preference for the edible component. As demonstrated hereinafter, these attractants include highly volatile sulfur containing compounds in the breath of the rodent. As used herein, the term "breath" includes mouth air, nose air and lung air of the subject rodent. These sulfur containing compounds include carbonyl sulfide and carbon disulfide, the latter of which is preferred since it is not a gas at room temperature.

Figure 1:
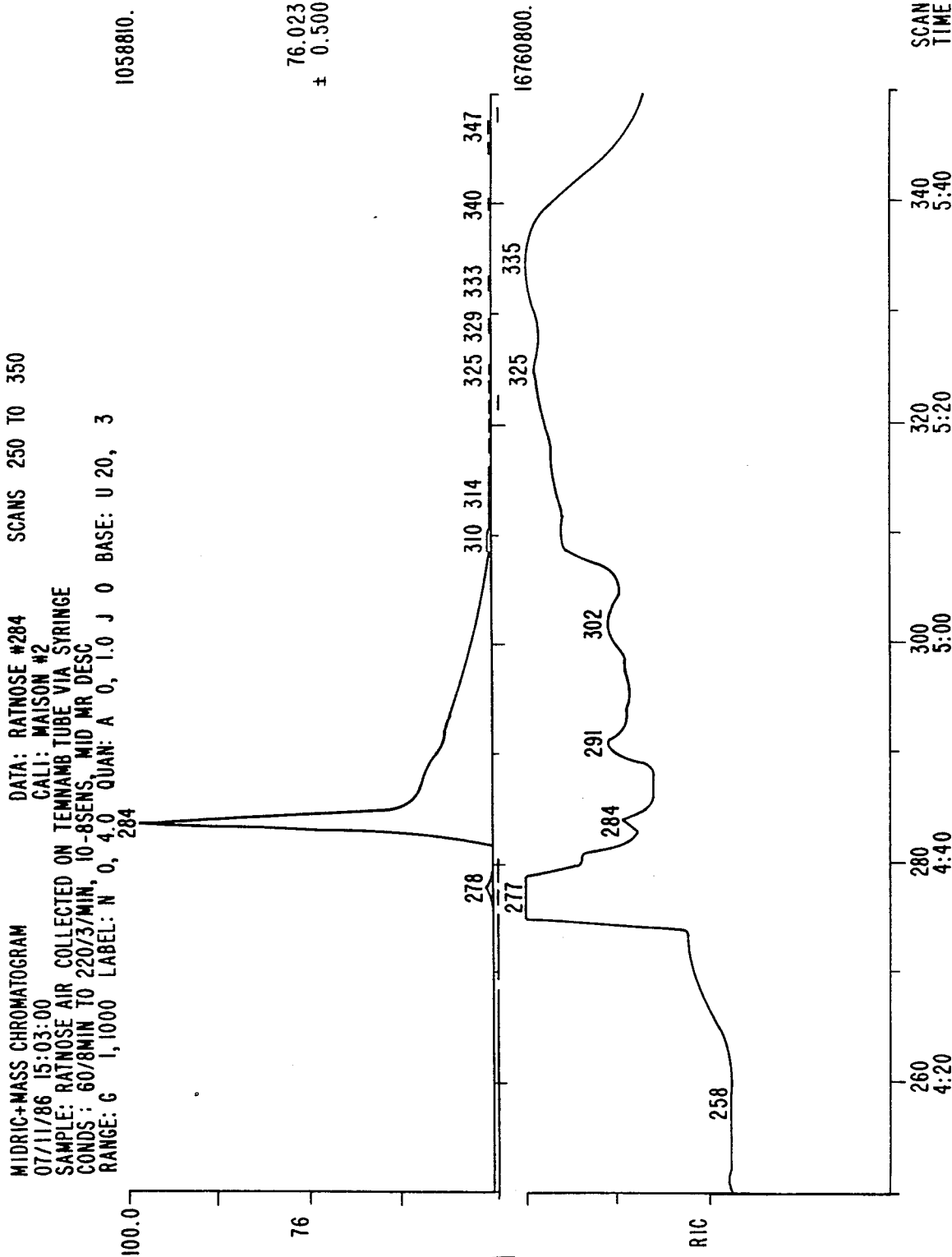
FIG. 1A is a computer generated mass chromatogram of collected breath from three rats.
FIG. 1B shows the plot of m/z 76, an anion characteristic of the carbon disulfide molecule. Chromatographic conditions are 60/8/min to 220/3/min.
Figure 2:
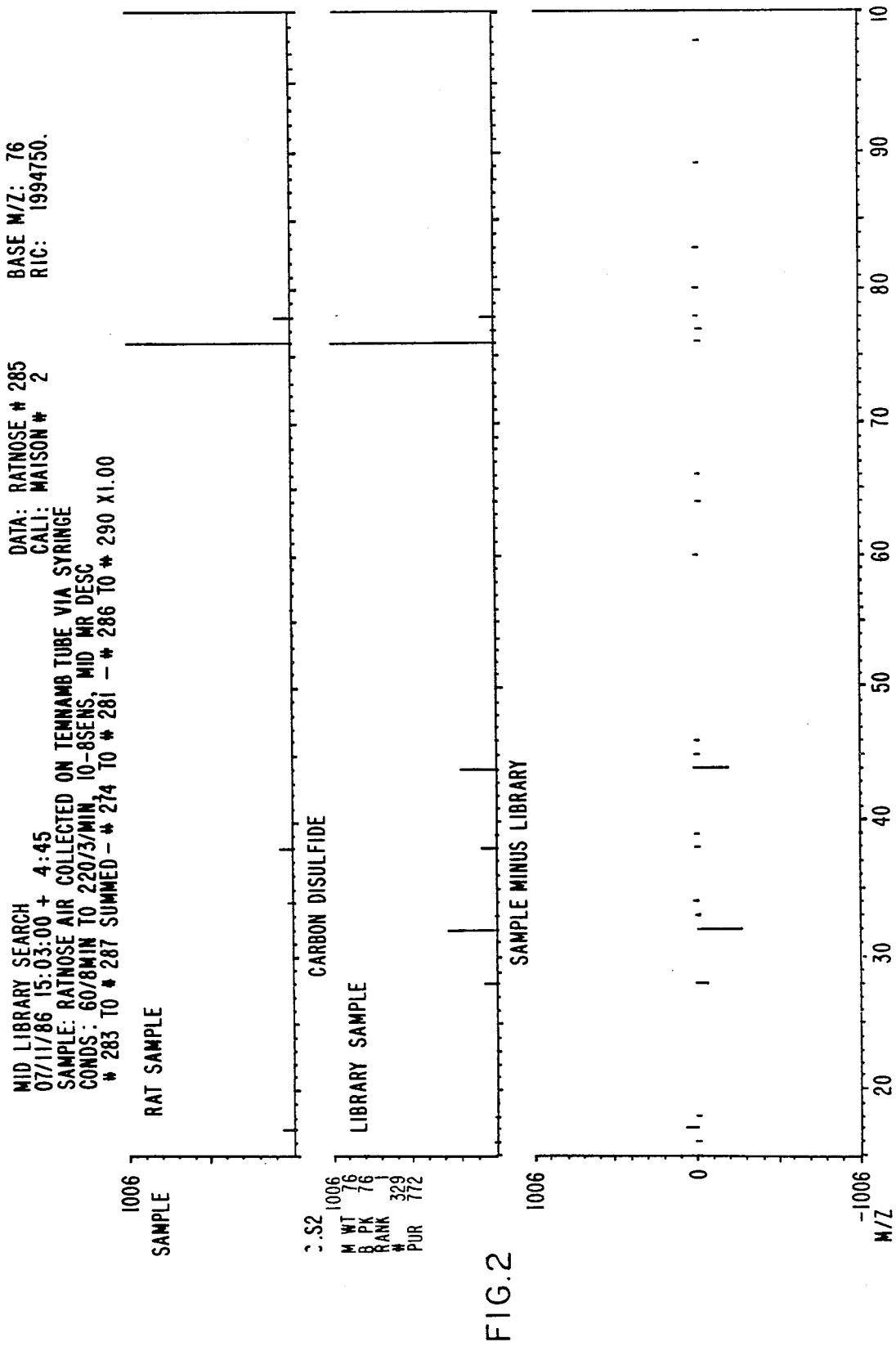
FIG. 2A shows a computer enhanced mass spectrum of carbon disulfide compared to the best fit (FIG. 2B) in the library.
FIG. 2C shows the enhanced spectrum minus the library spectrum for carbon disulfide. Enhancement of the spectrum of FIG. 1B around the peak maxima shows a mass spectrum characteristic of carbon disulfide, as seen in FIG. 2A. The data are interpreted disclosing that carbon disulfide is present in the combined breath sample.

FIG. 1B, are gc/mass spectra of rat nose air collected on Tenax tube via syringe. The figures indicate that carbon disulfide is present on the breath of the subject rodents. Other data (not presented in the figures) similarly indicates the presence of other highly volatile sulfur compounds, particularly carbonyl sulfide. From the data currently available, carbon disulfide appears to be the principle constituent responsible for the effects observed herein, other highly volatile sulfur containing compounds may also act in combination with carbon disulfide to produce the observed effect. The presence of sulfur containing compounds in the breath of rodents is not surprising, since sulfur containing compounds are present in the breaths of many species, including human. Indeed, sulfur containing compounds, which are volatile and pungent, are the principle compounds associated with halitosis in humans. What is surprising, however, is that the particular sulfur containing compounds are interpreted by rodents as a "safe" or desirable signal which will cause them to exhibit a marked preference for food which is associated with such attractants. At least in the human, such odors are not considered attractive or appetizing.

It is interesting to note that it is possible to condition the rodent by pairing attractant and a given edible so that he will exhibit a preference for the edible even though the particular sample of that edible which he may then consume does not contain the attractant. Accordingly, the present invention provides a novel method of conditioning a rodent to prefer a selected rodent edible comprising the steps of providing the sample of the rodent edible together with a sample of the attractant naturally present in the breath of that rodent, and exposing that rodent to be conditioned to combined amounts of those samples effective to condition the rodent to preferentially select said edible for consumption.

For the purpose of proving the efficacy of the subject invention, as well as for demonstrating various manners in which it may be employed, applicants conducted the following experiments.

EXAMPLE No. 1

A solution of 1 ppm of reagent grade carbon disulfide ($CS_2$) in distilled water was prepared. A rodent edible, in this case normal 5 gram feed pellets (Wayne Lab Blox, an ordinary rat chow) were treated with three drops of the $CS_2$ solution per pellet or three drops of distilled water ($dH_2O$). Four adult male Sprague-Dawley derived Norway rats (age approximately two months) were then given an opportunity to choose between $CS_2$ treated pellets and $dH_2O$ treated pellets on each of four consecutive days. All four rats, in every case, investigated the $CS_2$ treated and $dH_2O$ treated pellets, and expressed a clear and statistically significant preference for the $CS_2$ treated pellets, taking each one of them back to its eating area for consumption or storage before taking any of the otherwise identical pellets back to its eating area for storage or consumption (p less than 0.003). These results demonstrate that $CS_2$ is a powerful attractant, and that it will stimulate a preference even between otherwise identical samples of a rat's normal diet.

EXAMPLE No. 2

A study was conducted to confirm the hypothesis and finding that $CS_2$ is a powerful attractant. In addition to the test reported above, which is consistent with this hypothesis, the following test was performed. Observers were caused to interact with a surrogate rat, one end of which was rolled in Diet $N_1$ and wetted with $CS_2$. The procedure for preparation and presentation were substantially similar to those reported in *Animal and Learning Behavior*, 13: 31–38 (1985) which is incorporated herein by reference. In a subsequent choice between Diets $N_1$ and $N_2$, the observer preferred $N_1$. The following is a more detailed report of the experimental conditions relating to this test: Twenty-four female Long-Evans rats were randomly assigned to four conditions: cinnamon control, cocoa control, cinnamon experimental and cocoa experimental. Each subject was individually housed. Each rat was allowed to interact for 30 minutes with a surrogate demonstrator in the apparatus illustrated in Galef et al, *Animal and Learning Behavior*, 13: 31–38 (1985) which has been incorporated herein by reference. Surrogate demonstrators were rat-sized constructions of cotton batting stuffed in a surgical gauze tubes. One end of each demonstrator was rolled in either cinnamon-flavored or cocoa-flavored diet and anointed with three drops of fluid. Each subject in each experimental group interacted for 30 minutes with a surrogate rolled in either cinnamon or cocoa-flavored diet anointed with three drops of $CS_2$ (1 ppm in distilled water). Each subject in each control group interacted for 30 minutes with a surrogate rolled in either cinnamon or cocoa flavored diet anointed with three drops of distilled $H_2O$.

Immediately upon termination of interaction, each subject in this experiment was returned to its home cage and allowed to choose between cinnamon and cocoa-flavored diets for 22 hours. The following table sets forth the results:

| 1 | CONTROL ($dH_2O$) | | EXPERIMENTAL ($CS_2$-1 ppm) | |
|---|---|---|---|---|
|   | Cin | Coc | Cin | Coc |
| n | 6 | 6 | 6 | 6 |
| X | 45.3% | 55.8% | 80.1% | 49.4% |
| SEM | 16.3% | 7.4% | 5.6% | 13.6% |

In the above table, entry number 1 indicates the diet, "Cin" being cinnamon, "Coc" being cocoa, in which the surrogate was rolled. Entries in the table equal the mean percentage of total intake by subjects during the 22 hour test that was cinnamon flavored diet. Note that the observers in the control groups were not influenced by the diet their surrogates were rolled in. Observers in the experimental group exposed to the Cin surrogates were influenced by the diet their surrogates were rolled in. Observers in the experimental group exposed to the Coc surrogates were not so influenced. Subsequent investigations suggested that this lack of effect was caused by the evaporation of $CS_2$ from the Coc surrogates prior to presentation to observers, since there is thought to have been about a thirty minute delay between $CS_2$ application and presentation.

EXAMPLE 3

To test the effect of carbon disulfide as an attractant for other rodent species, 5 grams food pellets were treated with three drops of 1 ppm $CS_2$ in distilled water or distilled water ($dH_2O$). Ten mice which were not food deprived, were individually presented with two cups, one containing two 5 gram food pellets treated with $CS_2$, and the other containing $dH_2O$ treated pellets.

After one hour, only five had touched any of the pellets presented to them. Of those five, two mice took all of the $CS_2$ treated pellets and none of the $dH_2O$ treated pellets. Two took one $CS_2$ treated pellet and no $dH_2O$ treated pellets, and the fifth took one $dH_2O$ treated pellet. Accordingly, these data indicate that volative sulfur compounds such as $CS_2$ also act as attractants in other rodent species, such as mice.

As seen from the above, sulfur containing compounds such as carbon disulfide will increase the preference which a rodent shows for a subject edible. Since carbon disulfide is highly volatile at room temperatures, it is anticipated that commercial food or bait preparations may require preparation techniques intended to extend the persistency of these odors. Many techniques are known to the art for extending the persistency of odors. For example, the persistency of highly volatile odors can be extended through microencapsulation techniques, or other techniques such as at least partially entrapping the subject materials in a film former. For example, the subject materials may be entrapped by spray drying in a film forming material, such as a modified food starch, which will extend the persistency of the subject volatile sulfur containing compounds. Obviously, when carbonyl sulfide is the preferred attractant, other techniques at preserving its persistency should be employed since carbonyl sulfide is a gas at room temperature. In either event, the amount of volatile material remaining associated with the edible component should be sufficient to significantly alter the preference of the rodent for caching and/or eating the subject edible.

The above-identified experiments clearly indicate that certain sulfur containing compounds present in the breath of rodents can dramatically effect the preference which those rodents show for edibles associated therewith. Accordingly, novel and improved edibles, such as foods, baits, tracking powders, etc., as well as novel methods for effecting the preference shown by rodents for certain foods, are provided by the present invention.

We claim:

1. A rodent edible for feeding to rodents comprising:
   (a) an edible component selected from the group consisting of a poison, a sterilant, a food, a bait and tracking powder, and
   (b) a rodent attractant naturally present in the breath of said rodents selected from the group consisting of carbon disulfide and carbonyl sulfide in an amount effective to increase the preference for said edible component to said rodents.

2. The edible of claim 1 wherein said attractant is carbon disulfide.

3. A method of conditioning a rodent to prefer a rodent edible selected from the group consisting of a poison, a sterilant, a food, a bait and tracking powder, comprising feeding said rodent an amount of a composition comprising said rodent edible and a rodent attractant naturally present in the breath of said rodent selected from the group consisting of carbon disulfide and carbonyl sulfide, said amount of rodent attractant being an amount effective to condition said rodent to preferentially select said edible.

4. The method of claim 3 wherein said rodent attractant is carbon disulfide.

5. A method of increasing the palatability of a given rodent edible to a rodent comprising the step of applying carbon disulfide to said edible in an amount effective to increase the palatability of said edible to said rodent.

* * * * *